United States Patent [19]
Marini et al.

[11] Patent Number: 4,637,820
[45] Date of Patent: Jan. 20, 1987

[54] COPPER-MODIFIED CARBOXYALKYL-CELLULOSE FIBER

[75] Inventors: Ingo G. Marini, Lenzing, Austria; Scarlet Sustmann, Viersen, Fed. Rep. of Germany

[73] Assignee: Lenzing Aktiengesellschaft, Lenzing, Austria

[21] Appl. No.: 708,139

[22] Filed: Mar. 4, 1985

[30] Foreign Application Priority Data

Mar. 6, 1984 [DE] Fed. Rep. of Germany ....... 3408131

[51] Int. Cl.$^4$ ............................ D01F 1/10; D01F 2/24
[52] U.S. Cl. .......................................... 8/129; 536/98; 536/101
[58] Field of Search ....................... 8/129; 536/98, 101

[56] References Cited

U.S. PATENT DOCUMENTS

| 2,856,330 | 10/1958 | Vagemus | 427/439 |
| 4,043,952 | 8/1977 | Ganslaw et al. | 525/360 |
| 4,076,663 | 2/1978 | Masuda et al. | 527/312 |
| 4,090,013 | 5/1978 | Ganslaw et al. | 525/366 |
| 4,311,833 | 1/1982 | Namikoshi et al. | 536/98 |
| 4,385,632 | 5/1983 | Odelhog | 428/342 |
| 4,508,895 | 4/1985 | Balser | 536/98 |
| 4,579,943 | 4/1986 | Kamide et al. | 536/98 |

FOREIGN PATENT DOCUMENTS 1196407 6/1970 United Kingdom .

Primary Examiner—A. Lionel Clingman
Attorney, Agent, or Firm—Ernest G. Szoke; Henry E. Millson, Jr.; Mark A. Greenfield

[57] ABSTRACT

A modified fibrous material comprising cellulose fibers substituted at their cellulose anhydroglucose units by anionic moieties of at least one of the formulae: $-PO_3H^{(-)}$; $-(CH_2)_n-PO_3H^{(-)}$; $-(CH_2)_n-SO_3^{(-)}$; or $(CH_2)_n-COO^{(-)}$; where n is from 1 to 3; and capped by copper cations to the extent that said cellulose fibers bind from about 0.1 to about 3.0% by weight of copper, based on the weight of said fibers; as well as processes for its production.

22 Claims, No Drawings

COPPER-MODIFIED CARBOXYALKYL-CELLULOSE FIBER

BACKGROUND OF THE INVENTION

1. Field of the Invention

This invention relates to a copper-modified cellulose fibrous material which is water absorbent and possesses deodorizing and microbistatic properties. Fibrous materials such as these are of considerable value for numerous medical, hygienic, cosmetic and esthetic applications.

2. Statement of the Related Art

It is known that, in articles applied to the surface of the body, particularly in areas of the body where perspiration is heavy or where bodily secretions, such as blood or urine, are discharged, bacterial decomposition of the secretion occurs after only a short time under the effect of ubiquitously present bacteria. This bacterial decomposition is accompanied by the emission of unpleasant odors and, in many cases, leads to dangers through the growth of pathogenic microbes.

Accordingly there have been numerous attemps to provide fibrous materials with microbistatic and deodorizing properties. Known microbicides and deodorants, such as iodine, phenols, thiophenols, quaternary ammonium compounds, antibiotics, nitro compounds, formaldehyde and heavy metal compounds, have been proposed for this purpose. One of the greatest problems in this regard is fixing the active substance to the fibers. Copper compounds have also been proposed for this purpose.

U.S. Pat. No. 4,385,632 (and corresponding German published application No. 31 35 410) describe an absorbent padding of nonwoven cellulose fibers or wadding which is sprayed with an aqueous solution of a copper salt or prepared from fibers or wadding pre-treated with such a solution. Disclosed suitable copper salts are the borate, sulphate, chloride, formate, oxalate, tartrate, citrate, lactate, and especially, the acetate. This known material is attended by various disadvantages. Thus, the copper salt is not uniformly distributed in the absorbent padding, some of the copper salt crystallizes out after drying (which gives rise to difficulties during processing of the fibrous material), and the copper salt dissolves in the presence of water, for example, in a wet diaper or in a damp tampon, and can thus reach the surface of the skin in relatively high concentrations and produce undesirable reactions.

Published European patent application No. 19,371 describes a blood-coagulating absorbent material which consists of a water-swellable, covalently crosslinked anionic polyelectrolyte, for example crosslinked carboxymethyl cellulose, which is treated with transition metal ions, such as with copper ions. Disclosed salts for treatment include copper chlorides, nitrates, sulphates, and acetates in one process, and copper carbonates, oxides or hydroxides in a second process. However, materials such as these are not usually fibrous or cannot readily be converted into fibers, wadding or nonwovens. It is disclosed that the materials may be processed with a fibrous carrier as a support when used in hygiene aids. Both the manufacture and also the processing of this material are difficult.

DESCRIPTION OF THE INVENTION

The present invention provides an absorbent fibrous material which has permanent deodorizing and microbistatic properties, i.e. which cannot be washed out, and which is easy to make and process.

This is achieved by an absorbent fibrous material which consists essentially of cellulose fibers modified by anionic salt-forming moieties and which contains copper chemically attached to the fibers through those anionic moieties. In the context of the invention, cellulose fibers are understood to be cellulose, cotton and/or viscose fibers.

Anionic salt-forming moieties may be incorporated in the cellulose molecule in various ways. Anionically modified cellulose fibers of this type are known and, in some cases, are also commercially available. Suitable cellulose fibers of the type in question are, for example, cellulose fibers which carry at least one of the moieties of the general formulae: $-PO_3H^{(-)}$; $-(CH_2)_n-PO_3H^{(-)}$; $-(CH_2)_n-SO_3^{(-)}$; or $(CH_2)_n-COO^{(-)}$; (where n may have a value of from 1 to 3) which are attached via the oxygen to the anhydroglucose units. Known cellulose derivatives of this type include: cellulose phosphate obtainable by esterifying cellulose with phosphoric acid; phosphonoethyl cellulose obtainable by etherifying alkali cellulose with chloroethyl phosphonate; phosphonomethyl cellulose obtainable by etherifying cellulose with chloromethyl phosphonate; sulfoethyl cellulose obtainable by etherifying cellulose with chloroethane sulfonate and the similarly obtainable sulfomethyl cellulose and sulfopropyl cellulose. Also useful is 1-sulfo-2-hydroxypropyl cellulose, which may be obtained by cellulose etherification with 1-chloro-2-hydroxypropane sulfonate.

Carboxyl groups may be introduced into the cellulose molecule in two basically different ways:

by the physical incorporation of carboxyl-containing compounds in the viscose, i.e. in a cellulose dissolved in the form of cellulose xanthogenate, to form incorporated viscose fibers (alloy fibers) or by the chemical reaction (etherification) of the fiber-forming cellulose with carboxyl-containing reagents to form cellulose fibers uniformly modified by, for example, carboxyalkyl groups corresponding to the formula $-(CH_2)_n\text{-COOH}$, in which n may have a value of from 1 to 3.

The physical incorporation of compounds containing carboxyl groups in the viscose is obtained, for example, by the addition of alkali salts of acrylic acid homopolymers, acrylic acid-methacrylic acid copolymers, methyl vinyl ether-maleic acid anhydride copolymers, alginic acid or carboxymethyl cellulose to the viscose solution, followed by spinning in the usual way into a precipitation bath. Commercially available fibers of this type include fibers which are a blend of viscose and acrylic acid-methacrylic acid copolymer sold by Enka under the trademark ABSORBIT. Fibers such as these are not uniformly modified, but instead are made up of modified and unsubstituted fiber fragments.

Cellulose fibers chemically modified throughout by carboxyalkyl groups are particularly preferred for producing the bacteriostatically treated fibrous materials of this invention. In fibers such as these, the entire fiber-forming cellulose is uniformly modified. They may be obtained by carboxymethylating cellulose fibers with sodium chloroacetate, immediately after conversion into alkali cellulose. The cellulose thus modified may be improved in its fiber structure by the viscose spinning process. However, a viscose fiber regenerated by the viscose spinning process may also be subsequently carboxymethylated with chloroacetic acid. A third possibility of obtaining cellulose fibers uniformly modifed with carboxyalkyl groups is to add sodium chloroacetate to the viscose solution during xanthogenation and then spin the carboxymethylated viscose in the usual way. Viscose fibers such as these, uniformly modified by carboxymethyl groups, are commercially available from Lenzing AG under the trademark VISCOSORB 1N.

If acrylonitrile is added to the viscose solution during xanthogenation, viscose fibers consisting of carboxyethyl cellulose having a low degree of substitution are obtained on completion of the viscose spinning process. Fibers such as these are commercially available from FMC Corporation under the trademark BAR (Bondable Avisco Rayon) fibers.

Other reagents suitable for uniformly modifying the viscose by addition to the viscose solution during xanthogenation are sodium vinyl sulfonate, sodium chloromethane sulfonate, and sodium chloromethane phosphonate. Uniformly chemically modified viscose fibers containing sulfoethyl groups, sulfomethyl groups and phosphonomethyl groups are obtained in this way.

However, a fibrous cellulose chemically modified throughout by carboxyl groups and, more especially, by carboxymethyl groups is particularly preferred for producing the fibrous material according to this invention. A fibrous material obtained from a carboxymethyl-modified cellulose regenerated by the viscose spinning process is expecially suitable.

The cellulose derivatives suitable for producing the fibrous material according to this invention should have such a high degree of substitution, based on the anionic salt-forming groups, that they are capable of binding from 0.1 to 3.0% by weight of copper, based on the weight of the fibrous material. The most suitable carboxymethyl-modified viscose fibers for the fibrous material according to the invention have a degree of substitution of from 0.01 to 0.3, i.e. they contain on average from about 0.01 to 0.3 carboxymethyl groups per anhydroglucose unit. The content of bound copper should make up from 0.2 to 2.0% by weight and preferably from 0.6 to 1.6% by weight of the fibrous material.

It has also proved to be of advantage for the fibrous material according to the invention to have a fiber pH-value, as measured in accordance with German Industrial Norm (DIN) 54,275, of from 4 to 5. The effect of a fiber pH of this order is that the fibrous materials according to the invention have a certain buffer effect on absorbed body liquids and thus establish a physiologically favorable, mildly acidic pH on the skin surface, so that inflammation and susceptibility to alkaliphilic microbial disorders are avoided.

Because the fibrous material according to the invention is particularly suitable for the production of sanitary hygiene aids, it should—in another preferred embodiment—have a high water retention capacity of at least 80%, as measured in accordance with DIN 53,814.

The fibrous material according to the invention may readily be produced from known fibers containing anionic salt-forming moieties by treating the fibers containing anionic salt-forming moieties with an aqueous cupric ($Cu^{+2}$) salt solution and washing the fibers with water until they are substantially free from salt, followed by drying.

The high water retention fibrous material preferably employed may readily be produced by using a carboxymethyl viscose fiber having a degree of substitution of from 0.01 to 0.3 and a correspondingly high water retention capacity. For example, the commercially available VISCOSORB 1S fibers (a trademark of Lenzing AG) having a water retention capacity of approximately 200% and a degree of substitution of about 0.10 may be used in the described process either in the sodium salt form or after conversion into the free acid form.

In producing the fibers of this invention, any cupric salt may be used, provided that it is water soluble, has an anion which can be displaced in an ion-exchange reaction with the anionic salt-forming moieties of the modified cellulose fibers, and is physiologically compatible. The anionic salt-forming moieties of the modified cellulose fibers are preferably capped with hydrogen cations, although other cations may be employed, depending upon the cupric salt used and the presence of an acid. The use of a physiologically compatible cupric salt is only important because residual traces of the cupric salt may remain in the cullulose fiber after treatment. Useful cupric salts are the chloride, nitrate, sulfate or acetate, or the carbonate, oxide, or hydroxide, depending upon the treatment method, with cupric sulfate being preferred! Of course, once the cupric cation is attached to the anionic moiety of the cellulose fiber, the manner of production is irrelevant to the finished fiber. A solution of from 1 to 20 g/l of $CuSO_4.5H_2O$ in water is one example of a particularly suitable aqueous cupric salt solution.

The treatment is generally carried out in the absence of heat for a period of from 1 to 60 minutes, 20 to 40 minutes being preferred. Thereafter, the copper salt solution is removed from the fiber, for example by pressing, the fiber is washed with water until the washing water is substantially free from sulfate ions, the water is removed from the fiber, by further pressing, and the fiber is dried in a stream of air. A fibrous material according to the invention having a fiber pH of from 4 to 5 may readily be obtained by this process providing a cupric salt solution adjusted to a pH-value of from 4 to 5 is used.

The fibrous material according to the invention has a more or less pronounced blue coloration, depending on the quantity of copper attached. This blue color, which cannot be washed out under practical conditions, is generally not unpleasant and is psychologically consistent with the perception of hygiene. Bacteria, particularly those encountered in the body's intimate regions, for example *Escherichia coli, Staphylococcus aureus* and *Candida albicans,* do not proliferate on the fibrous material according to the invention, even under optimal incubation conditions. Even after incubation for three days, nutrient cultures charged with the fibrous materials according to the invention did not emit the unpleasant characteristic odor of corresponding cultures charged with normal wadding. By virtue of the above-mentioned properties, the fibrous material according to the invention is suitable for numerous applications, particularly for medical, hygienic and aesthetic purposes, for example for surgical dressings, absorbent cotton, sweat pads, shoe liners, diapers, catamenial devices, and other absorbent disposalbe articles.

The invention is illustrated by the following Examples.

EXAMPLES

A. Production of the deodorizing and microbistatic fibrous materials according to the invention (Examples 1-4)

Examples 1 to 4 were produced from a commercially available, carboxymethylated viscose fiber (Viscosorb 1S, a trademark of Lenzing AG) characterized by the following technical data:

| Viscosorb 1 S | |
|---|---|
| Fiber pH | 7.0–7.5 (DIN 54,275) |
| Carboxyl group content | 2.3–2.7% by weight |
| Degree of substitution | 0.09–0.10 |
| Water retention capacity | 180–200% |

EXAMPLE 1

1 kg of Viscosorb 1S fibers was treated for 30 minutes at room temperature (20° C.) with 20 l of a solution of 20 g of $CuSO_4.5H_2O$ in 1000 ml of water of which the pH-value had been adjusted to pH 5 with dilute sulfuric acid. The fibers were then squeezed to a moisture content of 200% and washed with water until the washing water was free from sulfate. They were then squeezed again to a moisture content of around 200% and dried for 4 hours at 105° C. in a recirculating-air drying champer. The fibrous material obtained had the following data:

| Fiber pH | 5.6 (DIN 54,275) |
|---|---|
| Copper content | 1.45% by weight |
| Water retention capacity | 87% (DIN 53,814) |

EXAMPLE 2

The procedure was as in Example 1, except that the pH-value of the copper sulfate solution was adjusted to ph 4.
The fibrous material obtained had the following data:

| Fiber pH | 5.0 (DIN 54,275) |
|---|---|
| Copper content | 2.92% by weight |

EXAMPLE 3

1 kg of fibers (Viscosorb 1S) was converted into the acid form first by treatment with a 0.2% aqueous hydrochloric acid solution (for 30 minutes at room temperature) and then washing out the excess hydrochloric acid. The fibers squeezed to a moisture content of around 200% were then treated for 30 minutes at room temperature (20° C.) with a solution of 20 g of $CuSO_4.5H_2O$ in 1000 ml of water of which the pH-value had been adjusted to 4.5 with dilute sulfuric acid.

Working up was carried out in the same way as in Examples 1 and 2. The fibrous material obtained had the following data:

| Fiber pH | 4.5 (DIN 54,275) |
|---|---|
| Copper content | 1.65% by weight |
| Water retention capacity | 87.4% (DIN 53,814) |

EXAMPLE 4

The procedure was as in Example 3, except that the treatment was carried out using 5.0 g of $CuSO_4.5H_2O$.
The fibrous material obtained had the following data:

| Fiber pH | 4.2 (DIN 54,275) |
|---|---|
| Copper content | 0.64 |
| Water retention capacity | 109.5% (DIN 53,814) |

EXAMPLE 5 (Comparison Example)

1 kg of normal (unmodified) viscose fibers was treated in the same way as in Example 1. The fibrous material obtained had the following data:

| Fiber pH | 6.4 (DIN 54,275) |
|---|---|
| Copper content | 0.05% by weight |

B. Demonstration of the prevention of bacterial growth and of the deodorizing effect.

Germs tested:
 Staph. aureus
 E. Coli
 Ps. Aeruginosa
 Proteus mirabilis
 Candida albicans

Test Procedure

Quantities of 10 ml of CASO culture broth were added to quantities of 1 g of normal viscose (3.6 dtex, 30 mm) made by Hoechst and of the copper-impregnated fibrous material according to Examples 3 and 4 in test tubes. The test tubes thus prepared were inoculated with quantities of 0.1 ml of germ suspension (see above)
—24 h broth culture diluted in a ratio of 1:100—and incubated at 37° C.

Result

In the case of the normal viscose, growth occurred with each test strain (see above), whereas in none of the copper-impregnated fibrous materials could growth be detected, even after 72 h. At the same time, odor emission was only observed in the case of the cultures charged with normal viscose, corresponding to the normal broth cultures of the corresponding germs. The cultures charged with the special fibrous materials did not emit any odor.

We claim:
1. A modified fibrous material consisting essentially of viscose fibers modified by anionic moieties of the general formula:

wherein n is from 1 to 3;
which anionic moieties are each attached through an oxygen atom to a viscose anhydroglucose unit; wherein sufficient of said anionic moieties are present, and sufficient of said present anionic moieties are capped by copper cations, that said viscose fibers bind from about 0.1 to 3.0% by weight of copper, based on the weight of said fibers.

2. The modified fibrous material of claim 1 wherein the degree of substitution of said fiber by said anionic moiety is about 0.01 to 0.3.

3. The modified fibrous material of claim 1 wherein the bound copper content is about 0.2 to 2.0% by weight, based on the weight of said fibers.

4. The modified fibrous material of claim 1 wherein the bound copper content is about 0.6 to 1.6% by weight, based on the weight of said fibers.

5. The modified fibrous material of claim 2 wherein the bound copper content is about 0.2 to 2.0% by weight, based on the weight of said fibers.

6. The modified fibrous material of claim 2 wherein

7. The fibrous material of claim 1, having a fiber pH of about 4 to 5.

8. The fibrous material of claim 5, having a fiber pH of about 4 to 5.

9. The fibrous material of claim 6, having a fiber pH of about 4 to 5.

10. The fibrous material of claim 1, having a water retention capacity of more than 80%.

11. The fibrous material of claim 7, having a water retnetion capacity of more than 80%.

12. The fibrous material of claim 8, having a water retention capacity of more than 80%.

13. The fibrous material of claim 9, having a water retention capacity of more than 80%.

14. The modified fibrous material of claim 7 wherein said carboxyalkyl anions are carboxymethyl.

15. The modified fibrous material of claim 2 wherein said carboxyalkyl anions are carboxymethyl.

16. The modified fibrous material of claim 1 consisting essentially of viscose fibers uniformly modified by carboxymethyl anions, having a water retention capacity of approximately 200% and a degree of substitution of about 0.10.

17. A process for producing a modified fibrous material consisting essentially of viscose fibers substituted at their viscose anhydroglucose units by anionic moieties of the general formula: $(CH_2)_n$—$COO^{(-)}$; where n is from 1 to 3; and capped by copper cations to the extent that said viscose fibers bind from about 0.1 to about 3.0% by weight of copper, based on the weight of said fibers; said process comprising:
  treating viscose fibers uniformly substituted by said anionic moieties in their free acid form, with an aqueous solution of at least one cupric salt, in the absence of heat, for a period of about 1 to 60 minutes;
  washing said treated fibers with water until substantially all unreacted cupric salts and ion-exhange by-products are removed; and
  drying said treated fibrous material.

18. A process for producing a modified fibrous material consisting essentially of viscose fibers substituted at their cellulose anhydroglucose units by anionic moieties of the general formula: —$(CH_2)_n$—$COO^{(-)}$; where n is from 1 to 3; and capped by copper cations to the extent that said viscose fibers bind from about 0.1 to about 3.0% by weight of copper, based on the weight of said fibers;

said process comprising:
  treating viscose fibers uniformly substituted by said anionic moieties in the form of their alkali salts with sufficient acid to substantially convert said salts to their free acid form;
  further treating said viscose fibers with an aqueous solution of at least one cupric salt, in the absence of heat, for a period of about 1 to 60 minutes;
  washing said treated fibers with water until substantially all unreacted cupric salts, acid, and ion-exchange by-products are removed; and
  drying said treated fibrous material.

19. The process of claim 17 wherein: said substituted viscose fibers are carboxymethyl cellulose having a degree of substitution of about 0.01 to 0.3; and said cupric salt is cupric sulfate in an aqueous solution of from about 1 to 20 g/l.

20. The process of claim 18 wherein: said substituted viscose fibers are carboxymethyl cellulose having a degree of substitution of about 0.01 to 0.3; and said cupric salt is cupric sulfate in an aqueous solution of from about 1 to 20 g/l.

21. The process of claim 19 wherein said cupric sulfate solution is adjusted to a pH of about 4 to 5 before said treatment.

22. The process of claim 20 wherein said cupric sulfate solution is adjusted to a pH of about 4 to 5 before said treatment.

* * * * *